United States Patent [19]

Sokolovsky et al.

[11] Patent Number: 4,994,446
[45] Date of Patent: Feb. 19, 1991

[54] DRUG SYSTEM

[75] Inventors: Mordechai Sokolovsky, Tel Aviv; Yoel Kloog, Herzelia, both of Israel

[73] Assignee: Ramot - University Authority for Applied Research and Industrial Development Ltd., Tel Aviv, Israel

[21] Appl. No.: 293,136

[22] Filed: Jan. 3, 1989

[51] Int. Cl.5 .................... A61K 31/66; A61K 31/441
[52] U.S. Cl. ...................................... 514/75; 514/326
[58] Field of Search ................................. 514/75, 326

[56] References Cited

PUBLICATIONS

Chem. Abst. 108 126054n, (1988).
Chem. Abst. 110 128473p, (1989).

Primary Examiner—Stanley J. Friedman
Attorney, Agent, or Firm—Browdy & Neimark

[57] ABSTRACT

The invention relates to a drug system for the treatment and alleviation of the symptoms of epilepsy; as anticonvulsant agent, and for the prevention or alleviation of brain damage due to strokes. The drug system comprises as active ingredient a compound such as MK-801, phencyclidine or as thienyl-cyclohexyl-piperidine (TCP), which is administered in such a manner that it encounters and binds to the N-methyl-D-aspartate (NMDA) receptor channels. This is in the presence of glutamate or glycine, or similarly acting amino-acid, which is either present in the patient, or which can be administered separately. The effective drug can be effectively locked in the receptor channels by means of a glutamate antagonist, such as AP-5.

3 Claims, 2 Drawing Sheets

DRUG SYSTEM

FIELD OF THE INVENTION

The present invention relates to a novel drug system for use in the treatment of, and for the alleviation of the symptoms of a variety of diseases and states of ill-health in mammals, and especially in humans. Amongst others the drug system is of use an antiepileptic, as anticonvulsant, for the preparation or alleviation of brain damage caused by strokes etc.

The drug system is based on a combination of drugs of the MK-801 and PCP type, in combination with, or in sequential administration of certain excitatory amino acids, such as glutamate, glycine and aspartate, as well as related analogs, which substantially increase the rate of binding of the effective drug to the specific receptor. MK-801 is bound to the N-methyl-D-aspartate receptor, and it would seem that MK-801 acts as steric blocker of the NMDA channel. When a prolonged action of the drug is required, there is further administered an antagonist to such amino-acid, such as a glutamate antagonist, resulting in the freezing of the drug in the channel.

BACKGROUND OF THE INVENTION

The activity of PCP (phencyclidine) is discussed in NIDA Notes 2 (1987) 9. This article sets out the binding of PCP to two different receptors of the nerve membranes. MK-801, (+)-5-methyl-10,11-dihydro-5H-dibenzo-[a,d]-cyclohepten-5,10-imine maleate is known as potent anticonvulsant, and it is also known that MK-801 is a potent N-methyl-D-aspartate (NMDA) antagonist: Proc. Nat. Acad. Sci. U.S.A. 83 (1986) 7104. The kinetic characterization of the phencyclidine-NMDA receptor interaction, setting out evidence of a steric blockage of the channel was described in Biochem. 27 (1988) 843. It is known that there exist a number of excitatory amino acid antagonists, some of which block the neurotoxic activity of N-methyl-aspartate (NMDA). Amongst the most effective of these are phencyclidine (PCP) and MK-801, see Europ. J. Pharmac. 141 (1987) 357.

SUMMARY OF THE INVENTION

The present invention relates to a novel drug system which can be used in a variety of illnesses. The drug system is valuable as antiepileptic, anticonvulsant and agents that will prevent brain damage caused by strokes.

The novel system is based on a combination of an effective drug of the PCP and MK-801 and TCP (which is N[1-(2-thienyl)cyclohexyl]-piperidine, with a certain aminoacid or mixture of amino acids of the excitatory aminoacid type, such as glutamate, glycine and aspa-rate, and means for fixing the effective drug in a receptor channel, and means for the removal of the drug, if required, from such channel.

The active drugs (PCP, TCP, MK-801) seem to be steric blockers of the receptor channels, and especially of the NMDA channels. When administered simultaneously, or in a close sequence with glutamate, glycine or amino acids with the same type of activity, result in a considerable enhancement of the rate of binding of the drug-receptor complex. When it is desired to prolong the action of the drug, there is administered a suitable receptor antagonist, such as AP-5 which is a NMDA-receptor antagonist. This seems to inactivate the amino acid receptor, freezing the drug in the channel. The ratio of glutamate to TCP, for example, is of the order of $\mu$-molar of glutamate to 100 n-molar for TCP or MK-801. When the drug is already affixed in the receptor channels, and it is desired to terminate its activity, by its removal, there is administered an excess of glutamate, which again opens the channel, facilitating the exit of the drug, which is rapidly removed from said channels. Thus, when MK-801 is administered as antiepileptic drug or as agent to prevent stroke damage, it is administered with an excess of an amino acid such as glutamate, and after its entry into the receptor channel, it is blocked therein by the administration of an antagonist to such amino acid, such as the glutamate antagonist D-(−)2-amino-5-phospho-valeric acid, AP-5.

Similar results are obtained by the administration of PCP and TCP, in the presence of suitable amino acids adapted to open up the receptor channels. Kinetic and equilibrium binding experiments demonstrate that TCP and MK-801, as well as PCP are steric blockers of the channel.

BRIEF DESCRIPTION OF THE DRAWINGS

The accompanying drawings illustrate the invention. In such drawings.

Abbreviations phencyclidine (PCP); N[1-(2-thienyl)cyclohexyl]-piperidine (TCP); N-methyl-D-aspartate (NMDA); D(−)2-amino-5-phosphovaleric acid (AP-5); (+) 5 methyl-10,11 dihydro-5H-dibenzo[a,d]cyclohepten-5,10-imine maleate (dibenzocycloalkenimine) (MK-801).

Binding assays were performed in triplicate at 25° C. with repeatedly washed rat cerebral cortex membranes (80 $\mu$g protein) as described in Biochem. ibid. Assays were carried out in the absence or in the presence of $10^{-4}$ M AP-5, or in the presence of 10 $\mu$M MgCl$_2$ together with 1 $\mu$M L-glutamate and 1 $\mu$M glycine. Nonspecific binding was determined in samples containing $10^{-4}$ M PCP. Data were expressed as the specific binding of [$^3$H]MK-801 and analyzed according to the two-step binding model of interactions between noncompetitive blockers and the NMDA receptor channel. The model assumes a first order diffusion of the ligand from the outside into the interior of the channel, followed by association of the ligand with its receptor sites. Under the two extreme conditions employed here, viz., binding of [$^3$H]MK-801 in the presence of agonists (unlimited diffusion) and in the absence of agonists (limited diffusion) the time courses of receptor occupation should respectively follow pseudo first order (eq. 1) and first order (eq. 2) kinetics:

$$([RL]_{eq} - [RL])/[RL]_{eq} = \exp. -(k_1 k_2 [L]/k_b - k_{-1})t \qquad \text{eq. 1}$$

$$1 - \{K_d[RL]/[L](R_T) - [RL]\} = \exp. -K_b t \qquad \text{eq. 2}$$

where L, $R_T$, RLeq and RL are respectively the ligand, the total number of binding sites, the bound ligand at equilibrium and at time t. $k_a$ and $k_b$ are the forward and background diffusion constants; k1 and k_1 are the second order on-rate and the first order off-rate constants for the binding process. The overall equilibrium binding constant ($K_d$) is given by $K_{-1} \cdot k_b/k1 \cdot k2$.

Figure 1:
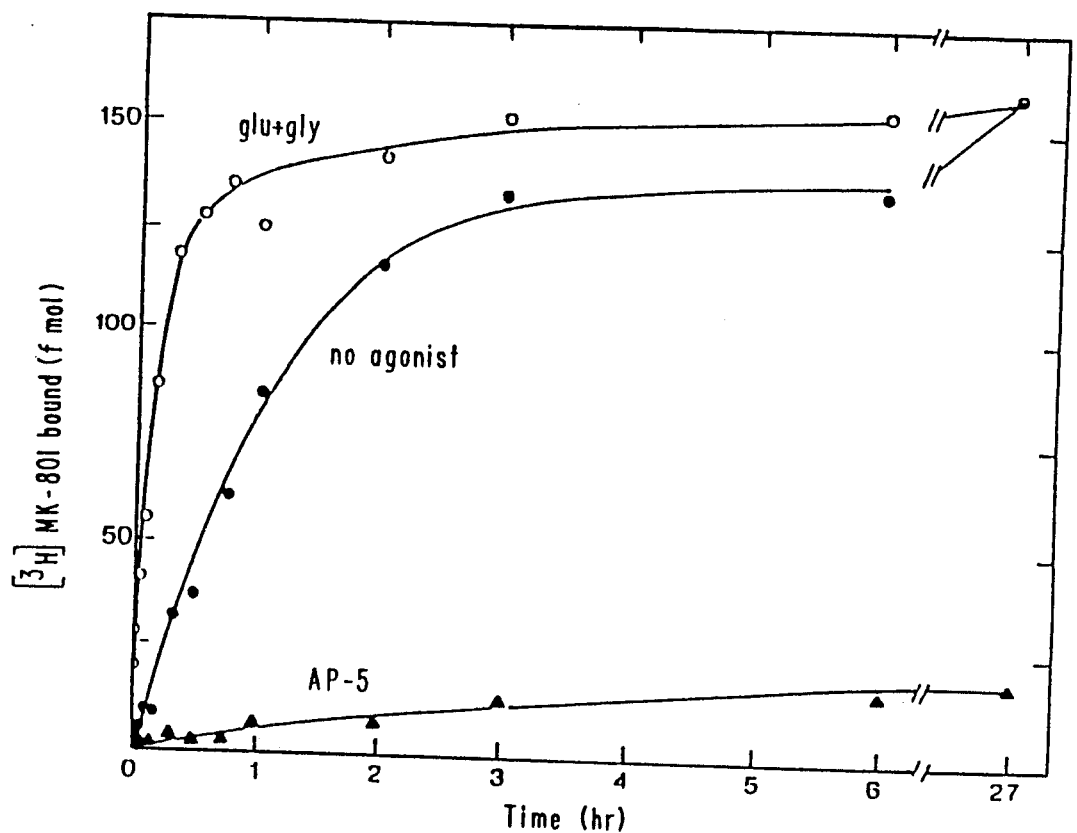
FIG. 1 is a graph that illustrate the time course of association of MK-801 with the NMDA receptor channel.
Figure 1A:
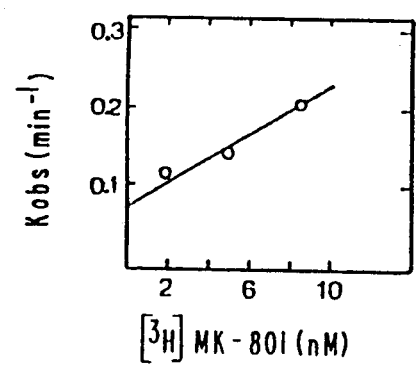
FIG. 1A is a graph that illustrates the increase in ligand-receptor binding as being time dependent.
Figure 1B:
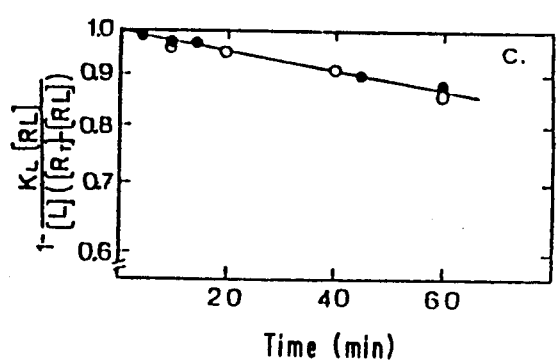
FIG. 1B is a graph that illustrates the observed time constants vary in a linear fashion with [$^3$H]MK-801 concentrations.
Figure 2A:
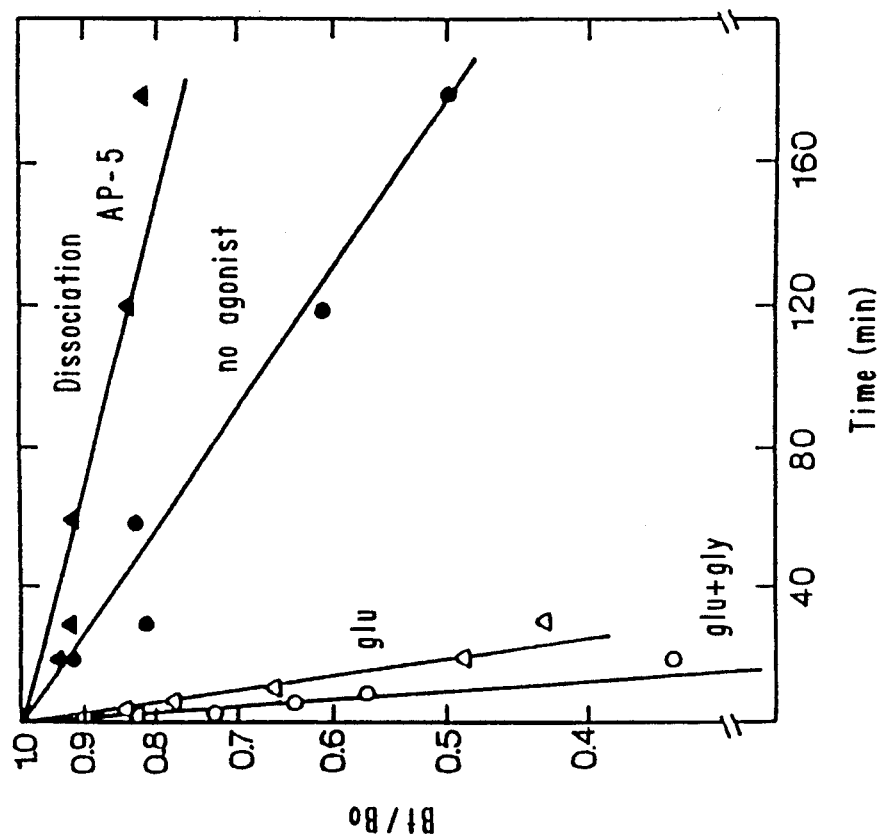
FIG. 2A is a graph that illustrates first order plots of the dissociation of MK-801 receptor complexes.
Figure 2:
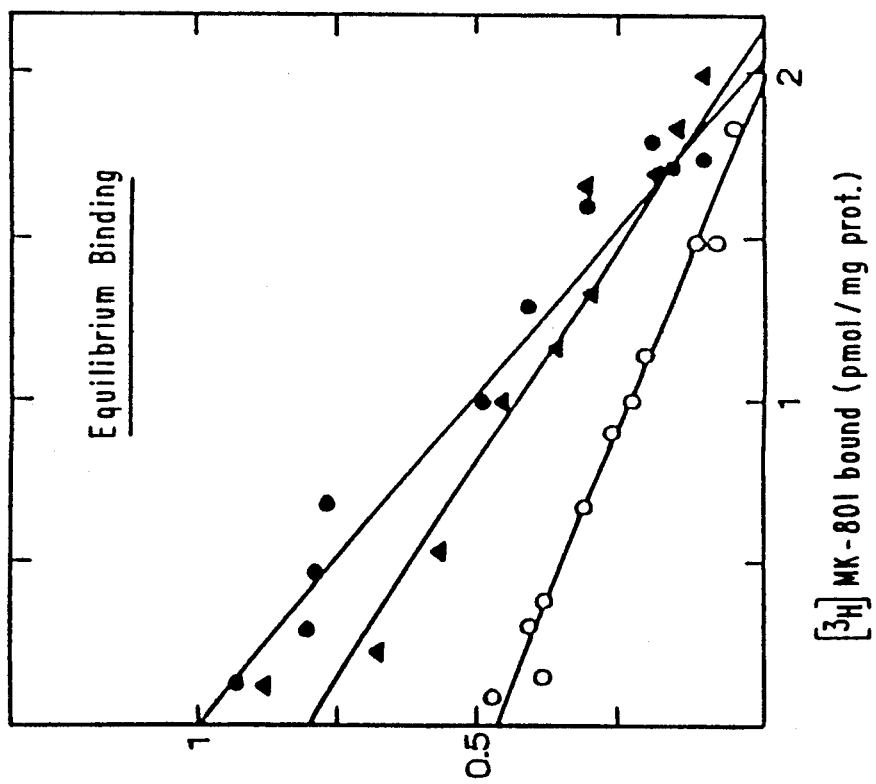
FIG. 2 is a graph that illustrates the equilibrium binding of MK-801.

FIG. 1A demonstrates typical time courses for [³H]MK-801-receptor association, with and without glutamate and glycine. The association rate of 5 nM [³H]MK-801 with the receptor in the absence of exogenous agonists was very slow (t½≃70 min) and reached equilibrium only after a prolonged incubation time (>6 hr). Upon addition of glutamate and glycine the rate of [³H]MK-801 binding to the receptor was markedly increased (t½≃7 min) and the reaction approached equilibrium within 45-60 min. The increase in ligand-receptor binding was time dependent; immediately after the onset of binding it was very high (~9 times that of the control) and then it declined (FIG. 1A). Similar time courses (not shown) were followed by 2 nM and 8.6 nM [³H]MK-801. The kinetics of [³H]MK-801 binding in the presence of glutamate and glycine followed a pseudo first order scheme (eq. 1): the observed time constants ($K_{obs}$) varied linearly with [³H]MK-801 concentrations (FIG. 1B), and the ratio between the apparent on-rate time constant ($1.55 \cdot 10^7$ M$^{-1}$ min$^{-1}$) and the apparent off-rate time constant (0.075 min$^{-1}$) was 4.8 nM. This kinetically derived dissociation constant ($K_d$) was similar to the $K_d$ for [³H]MK-801 determined at equilibrium in the presence (4.2 nM) and in the absence (2.1 nM) of glutamate and glycine (FIG. 2).

In the absence of exogenous agonists the kinetics of ligand-receptor association did not follow a pseudo first order scheme, as shown by the fact that the half times of the reactions (60-70 min) did not vary as a function of [³H]MK-801 concentration. These kinetics fitted well to the first order reaction scheme (eq. 2), and the observed time constant ($k_b$) derived from the kinetics of ligand receptor association ($2.28 \cdot 10^{-3}$ min$^{-1}$, FIG. 1C) was similar to the dissociation time constant obtained when receptor-ligand dissociation was measured in the absence of agonists ($5.5 \cdot 10^{-3}$ min$^{-1}$, FIG. 2). Also, the addition of 1 μM glutamate to [³H]-801-receptor complexes resulted in a marked increase in the dissociation rate (half time 18 min, compared to the control value of 180 min, FIG. 2) and the effect was enhanced by glycine (half time=4 min, FIG. 2). Consistency with the two-step binding model (see Methods) was further shown by the fact that the dissociation rate constant determined in the presence of glutamate and glycine (0.1 min$^{-1}$, FIG. 2) was similar to $k_{-1}$ value obtained under the same conditions during ligand-receptor association (0.075 min$^{-1}$, FIG. 1B). Taken together, the association and dissociation kinetics of [³H]-801 binding to the receptor suggest that in the absence of agonists the rate-limiting step is the diffusion of the outside ligand ($L_o$) into the interior ($L_c$) of the presumably closed NMDA receptor channel

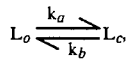

whereas in the presence of agonists this limitation is removed (presumably because the channel is open) and the rate-limiting step is the binding process itself.

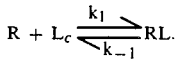

It should be noted, however, that the competitive NMDA-receptor antagonist, AP-5, by itself decreases the rates of [³H]-801-receptor association (FIG. 1A) and dissociation (FIG. 2) as compared to the control level, possibly indicating the presence of residual glutamate (or glycine) in the membrane preparation. It seems that AP-5 "freezes" the receptor in such a way that [³H]-801 is prevented from penetrating into the channel (see FIG. 1A) or dissociating from it (FIG. 2). Indeed, the addition of AP-5 to preequilibrated [³H]-801-receptor complexes did not alter the equilibrium binding (FIG. 2).

The kinetic results together with the equilibrium binding data indicate that glutamate and glycine affect mainly the rates of [³H]-801-receptor complex formation and dissociation, and not the maximal number of binding sites (FIG. 1A and FIG. 2) or $K_d$ (FIG. 2). Thus, in agreement with the electrophysiological data, [³H]-801 like [³H]TCP appears to act as a steric blocker of the NMDA-receptor channel and not as an allosteric effector.

The findings of this study have important therapeutic implications: the channel-ligand complexes formed following in vivo administration of MK-801 can be prevented from dissociating by a competitive antagonist (e.g. AP-5), which freezes the complex.

FIG. 1A illustrates the time course of association of [³H]-801 (5 nM) with the NMDA receptor channel. Binding was determined at 25° C. as a function of time in the absence (●) and in the presence of glutamate and glycine (○) or in the presence of AP-5 (▲); whereas 1B illustrates the observed time constants ($K_{obs}$) derived from the pseudo first order plots of the association of 2, 5 and 8.6 nM [³H]-801 in the presence of glutamate and glycine plotted as a function of the ligand concentration. FIG. 1C is a first order plot (eq. 2) of [³H]-801-receptor association in the absence of agonists determined with ligand concentrations of 2 nM (○) and 8.6 nM (●).

FIG. 2 left illustrates the equilibrium binding of [³H]-801. Binding of [³H]-801 as a function of its concentration was assayed after incubation for 4 hr at 25° C. in the absence (●) or in the presence (○) of glutamate and glycine. Also shown are data for [³H]-801 binding to the receptor measured after their incubation for 3 hr followed by an additional 1 hr of incubation in the presence of 100 μM AP-5 (▲). Data are expressed in the form of Scatchard plot.

FIG. 2 right shows first order plots of the dissociation of [³H]MK-801-receptor complexes. Samples were incubated at 25° C. with 8 nM [³H]-801 for 2 hr. The dissociation reaction was initiated by the addition of 100 μM unlabeled PCP. Data show the dissociation reaction without added agonists (●) and in the presence of 1 μM glutamate (△), 1 μM glutamate+1 μM glycine (○), or 100 μM AP-5 (▲). Reactions were terminated either immediately (zero time) or at the indicated times. $B_o$—amount of [³H]MK-801 bound at zero time. $B_t$—amount of [³H]-801 bound at time t.

Dosages of the channel blocking agents, such as [$^3$H]-801, PCP and TCP will generally be, when administered by injection, of the order of 0.2 mg/kg to about 10 mg/kg of patient weight.

The glutamate or similar agent will be administered so as to obtain open channels; if same is present in adequate excess, such administration may be unnecessary.

The antagonist to the amino acids, such as AP-5, will be administered (i.v.) in the order of from about 5 mg/kg to about 100 mg/kg.

In patients suffering from a variety of diseases, the level of the glutamate will be a high one. Generally this will be such that it will maintain the channels in an open state. In such cases the administration of glutamate will not be necessary. In order to anchor the drug in such channel, the competitive antagonist of the glutamate or similar amino acid type will be effected with a certain time delay, of the order of about 5 to 20 minutes after the drug.

Drugs of the [$^3$H]-801, PCP or TCP type will block the channels after a brief period of time which will be open due to the presence of the excess of glutamate; and the administration of AP-5 type antagonists will firmly anchor the drug in such channels. The administration of the AP-5 type compound may be repeated after a certain period of time in order to bring about a prolonged of the drug in the channel.

We claim:

1. A pharmaceutical composition for the treatment of epilepsy, for use as anticonvulsant and for the prevention of damage caused by strokes in mammals, including humans, which comprises in combination from 15 mg to 500 mg phencyclidine and from 350 mg to 1000 mg of D (−) 2-amino-5-phosphovaleric acid (AP-5).

2. A method for the treatment of epilepsy, for treating convulsions and for preventing the damage to the brain caused by a stroke, or at least for substantially reducing such damage, which comprises administering to the patient in need thereof a pharmacologically effective quantity of a pharmaceutical composition claimed in claim 1.

3. A method according to claim 2, where for the removal of the effective drug from the channel, there is administered an excess of glutamate.

* * * * *